United States Patent
Gay et al.

(10) Patent No.: US 6,455,621 B1
(45) Date of Patent: Sep. 24, 2002

(54) COMPOSITION BASED ON CALCIUM OF MAGNESIUM ACETYLACETONATE AND FREE OR CHELATED β-DIKETONES, PREPARATION AND USE

(75) Inventors: Michel Gay, Villeurbanne; Françoise Henrio, Morainvilliers, both of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/445,079
(22) PCT Filed: Jun. 4, 1998
(86) PCT No.: PCT/FR98/01142
§ 371 (c)(1), (2), (4) Date: Mar. 6, 2000
(87) PCT Pub. No.: WO98/55542
PCT Pub. Date: Dec. 10, 1998

(30) Foreign Application Priority Data

Jun. 4, 1997 (FR) .......................................... 97 06858

(51) Int. Cl.$^7$ ................................................ C08K 5/04
(52) U.S. Cl. ...................................... 524/398; 524/399
(58) Field of Search ................................. 524/394, 398, 524/399

(56) References Cited

U.S. PATENT DOCUMENTS 4,912,172 A * 3/1990 Hallgren ..................... 525/396
5,739,184 A * 4/1998 Marbry ....................... 523/403

* cited by examiner

*Primary Examiner*—Paul R. Michl

(57) ABSTRACT

The invention concerns a composition comprising calcium or magnesium acetylacetonate and at least a free β-diketone and/or in the form of a metal chelate, and having a melting point at most equal to 200° C. The invention also concerns the use of said composition for forming a formulation comprising at least a halogenated polymer, to prevent heterogeneity resulting from the presence of calcium or magnesium acetylacetonate, in said polymer.

17 Claims, No Drawings

COMPOSITION BASED ON CALCIUM OF MAGNESIUM ACETYLACETONATE AND FREE OR CHELATED β-DIKETONES, PREPARATION AND USE

This application is an application under 35 U.S.C. Section 371 of International Application No. PCT/FR98/01142, filed on Jun. 04, 1999.

The present invention relates to a composition comprising magnesium or calcium acetylacetonate and at least one β-diketone in free form or in the form of a metal chelate.

It likewise relates to the use of β-diketones in free form and/or in the form of their metal chelates as agents serving to improve the dispersion of magnesium or calcium acetylacetonate in formulations for halogenated polymers.

Calcium acetylacetonate is one of the well-known heat stabilizers for formulations comprising halogenated polymers, and more particularly polyvinyl chloride.

However, although it is clearly established that the halogenated polymer formulations can be effectively stabilized with respect to temperature, it nevertheless remains the case that the utilization of polymers stabilized in this way exhibits a number of difficulties. It has been found, in fact, that the presence of this specific chelate has been the cause of defects in the shaped polymer. More particularly, it has been noted that the articles obtained may exhibit heterogeneities having the appearance of craters, seeds or else pinholes.

Without wishing to be limited by such an explanation, it appeared that the origin of these defects in the shaped article lies in the fact that calcium acetylacetonate is very difficult to disperse homogeneously within the polymeric formulation. In fact, under the conditions in which formulations based on halogenated polymers are shaped, calcium acetylacetonate is present neither in dissolved form nor in melted form.

The same type of difficulty is anticipated with magnesium acetylacetonate.

One of the aims of the present invention is therefore to provide a solution to the problems of the heterogeneities which appear during the shaping of formulations which are based on halogenated polymers and stabilized by means of magnesium or calcium acetylacetonate.

It has been found, entirely unexpectedly, that a composition comprising the combination of magnesium or calcium acetylacetonate with at least one β-diketone in free form and/or in metal chelate form, the said β-diketone being selected such that the melting point of the resulting composition is not more than 200° C., makes it possible to overcome the problems described hereinabove. One of the first consequences of this composition is that its melting point is lower than that of calcium or magnesium acetylacetonate alone. It is recalled that the melting point of calcium acetylacetonate is approximately 250° C. and that of magnesium acetylacetonate is approximately 270° C.

There is a certain advantage in this owing to the fact that, during the utilization of the polymeric formulation, at temperatures which are commonly of the order of 200° C., the composition according to the invention, i.e. comprising magnesium or calcium acetylacetonate and the β-diketone in free or chelated form, is itself in melted form.

Furthermore, despite the fact that there is nothing to suggest so, the use of this particular mixture, prepared at the time of use, in halogenated polymer formulations makes it possible to improve considerably the homogeneity of the dispersion of magnesium or calcium acetylacetonate, such that the defects which appear when the polymer is shaped are eliminated.

Therefore, a first subject of the present invention consists of a composition having a melting point of less than or equal to 200° C. and comprising magnesium or calcium acetylacetonate and at least one free β-diketone of the following formula (I):

in which $R^1$ and $R^3$ are identical or different and represent a substituted or unsubstituted linear or branched $C_1$–$C_{30}$ hydrocarbon radical and $R^2$ represents a hydrogen atom or a linear or branched $C_1$–$C_4$ hydrocarbon radical; and/or at least one β-diketone in the form of a lanthanum, magnesium, aluminium, zinc or calcium chelate of the formula (II)

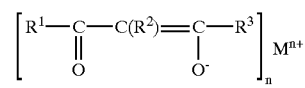

in which $R^1$, $R^2$, and $R^3$ are as defined above, $M^{n+}$ represents one or more of the abovementioned metals, n being 2 or 3, with the exception of the acetylacetonates of calcium and of magnesium.

A further subject of the invention is a process for preparing the said composition, which consists in contacting magnesium or calcium acetylacetonate and the β-diketone in free form or in chelate form in a mixer which allows the compounds to be homogenized and, if necessary, ground.

A further subject of the present invention consists in the use of the abovementioned composition as a heat stabilizer in halogenated polymer formulations.

Lastly, a final subject of the invention is the use of the said composition in the shaping of a formulation comprising at least one halogenated polymer for the purpose of preventing the appearance of heterogeneities due to the presence of magnesium or calcium acetylacetonate in the said polymer.

Other features and advantages of the present invention would appear more clearly, however, on reading the following description and examples.

As mentioned hereinabove, the composition according to the invention comprises magnesium or calcium acetylacetonate.

The acetylacetonate forming part of the present invention corresponds to the formula $[CH_3COCHCOCH_3]_2M.xH_2O$, in which x is between 0 and 2 and M represents calcium or magnesium.

Calcium acetylacetonate is well known and is found in commerce, for example, under the names Rhodiastab X7®, marketed by Rhodia Chimie.

In the text below, reference will be made only to calcium acetylacetonate, in awareness of the fact that the present invention is not limited to this single acetylacetonate but relates additionally to magnesium acetylacetonate or the combination thereof.

In accordance with the present invention, calcium acetylacetonate is combined with at least one β-diketone, which can be alternatively in free form, in the form of a metal chelate or in the form of a mixture of these two species.

Therefore, when the β-diketone is in a free form, it corresponds to the formula (I) $R^1COCHR^2COR^3$, in which $R^1$ and $R^3$, which are identical or different, each represent a substituted or unsubstituted, linear or branched $C_1$–$C_{30}$ hydrocarbon radical and $R^2$ is a hydrogen atom or a linear or branched $C_1$–$C_4$ hydrocarbon radical.

When the β-diketone is in the form of a metal chelate, it can be represented by the formula (II)

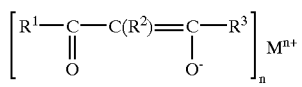

in which $M^{n+}$ represents at least one of the following metals: calcium, zinc, aluminium, magnesium or lanthanum, n being 2 or 3, $R^1$ and $R^3$, which are identical or different, represents a substituted or unsubstituted linear or branched $C_1-C_{30}$ hydrocarbon radical and $R^2$ represents a hydrogen atom or a linear or branched $C_1-C_4$ hydrocarbon radical, with the exception of the acetylacetonates of calcium and of magnesium.

In one more specific embodiment of the invention, the radicals $R^1$ and $R^3$, which are identical or different, represent a linear or branched $C_1-C_{24}$ alkyl or alkenyl radical; a $C_6-C_{30}$ aryl radical substituted or unsubstituted by at least one alkyl radical and/or one halogen atom and/or one silicon atom; or a $C_3-C_{14}$ cycloaliphatic radical which can, if desired, contain carbon—carbon double bonds.

Preferably, the radicals $R^1$ and $R^3$, which are identical or different, represent a linear or branched $C_1-C_{18}$ alkyl radical; a $C_6-C_{10}$ aryl radical substituted or unsubstituted by at least one alkyl radical and/or one halogen atom; or a $C_3-C_{14}$ cycloaliphatic radical which can, if desired, contain carbon carbon double bonds.

In a different embodiment, the said radicals $R^1$ and $R^3$ can be linked to one another such that the β-diketone compound is in the form of a ring system.

The above-described radicals $R^1$ and $R^3$ can be optionally modified (substituted) by the presence in the aliphatic chain of one or more groups of formula —O—, —CO—O—, —CO—.

The radical $R^2$ can be either a hydrogen atom or a $C_1-C_4$ alkyl radical whose aliphatic chain can be interrupted (substituted) by one or more groups of formula —O—, —CO—O—, —CO—.

Preferably, $R^2$ represents a hydrogen atom.

It should be noted that, if the β-diketone is present in the two abovementioned forms, the radicals $R^1$, $R^2$ and $R^3$ can be different from one product to the other.

The β-diketones can be obtained in accordance with conventional methods.

For example, the β-diketones can be synthesized using a condensation reaction of an ester with a ketone in the presence of an alkali metal agent which can be an amide of a cation such as sodium.

This reaction has been described in particular in the following publications: R. Hauser et al., "*The acylation of ketones to form diketones*", Organic Reactions—Vol. VII, Chapter 3, pp. 59–196, John Wiler, Ed., New York (1954); Wiedman et al., C. R. 238 (1954), p. 699; Morgan et al., Ber. 58 (1925), p. 333; Livingstone et al., *Am. Soc.* 46 (1924), pp. 881–888; R. Levine et al., *Am. Soc.* 67 (1945), pp. 1510–1517, and in European Patent EP 596 809.

By way of example of β-diketones suitable for the utilization of the invention, mention may be made in particular, with no intention of limitation thereto, of octanoylbenzoylmethane, stearoylbenzoylmethane, palmitoylbenzoylmethane, lauroylbenzoylmethane, dibenzoylmethane or else acetylbenzoylmethane, alone or in a mixture. It should be noted that it is possible to utilize the purified products or non-purified products.

As far as the non-purified products are concerned, reference may be made regarding the definition of the compounds, and also for the process for preparing them, to the abovementioned patent.

The following commercial products can be utilized advantageously in the present invention: Rhodiastab 50®, Rhodiastab X5®, Rhodiastab 83®, Rhodiastab X2®, which are marketed by Rhodia Chimie.

The compounds in chelate form are also known products and can be obtained by reacting the β-diketone in question with salts of the abovementioned metals, such as, in particular, the chlorides, sulphates and nitrates, with oxides or hydroxides, with the metal itself, with carbonates or else with alkoxides. It should be noted that these methods are described in particular in the work "*Metal β-diketonates and allied derivatives*" by R. C. Mehrota, R. Gaur, D. P. Gaur, Academic Press, 1978.

The chelates of octanoylbenzoylmethane, stearoylbenzoylmethane, palmitoylbenzoylmethane, lauroylbenzoylmethane, dibenzoylmethane, acetylbenzoylmethane or else acetylacetone (with the exception of the acetylacetonates of calcium or of magnesium), alone or in a mixture, can be used advantageously.

The chelates of zinc are very particularly advantageous.

In accordance with one preferred embodiment, the composition according to the invention comprises a β-diketone in the form of a chelate and, more preferably still, in the form of a zinc chelate.

As mentioned hereinabove, the melting point of the composition according to the invention is less than or equal to 200° C. and preferably less than or equal to 180° C.

Furthermore, in the composition according to the invention, the weight ratio between the magnesium or calcium acetylacetonate and the β-diketone in free form, or in chelate form, or else in the form of both of the latter is more particularly between 1/10 and 10/1, preferably between 1/6 and 6/1.

The composition according to the invention is obtained by any conventional means. In accordance with one particular embodiment, the composition according to the invention is obtained by contacting calcium acetylacetonate and the β-diketone in free form or in chelate form in a mixer which allows the compounds to be homogenized and, if necessary, ground.

Generally, the reagents are contacted in a high-speed paddle mixer.

The contact duration is generally sufficient for physicochemical interactions to be established between the various constituent elements of the composition. By way of illustration, this duration ranges from 10 minutes to one hour.

The temperature at which the acetylacetonate and the β-diketone are contacted varies between ambient temperature (20° C.) and 100° C. It should be noted that the temperature depends on the nature of the β-diketone and on the form in which it is present.

More particularly, a composition is obtained which is present in the form of a powder.

Advantageously, the composition according to the invention can be used as a heat stabilizer in halogenated polymer formulations.

The polymers in question are, more particularly, chlorinated polymers.

The invention is particularly appropriate to the stabilization of formulations based on polyvinyl chloride (PVC).

By polyvinyl chloride is meant compositions whose polymer is a homopolymer of vinyl chloride. The homopolymer can be modified chemically by means, for example, of chlorination.

Many copolymers of vinyl chloride can also be stabilized using the composition according to the invention. These are, in particular, polymers obtained by copolymerization of vinyl chloride with monomers having an ethylenically polymerizable bond, such as, for example, vinyl acetate, vinylidene chloride; maleic acid, fumaric acid or esters thereof; olefins such as ethylene, propylene and hexene; acrylic or methacrylic esters; styrene; and vinyl ethers such as vinyl dodecyl ether.

Customarily, the copolymers contain at least 50% by weight of units of vinyl chloride, and preferably at least 80% by weight of such units.

PVC, alone or in a mixture with other polymers, is the chlorinated polymer which is used most widely in the formulations stabilized in accordance with the invention.

Generally speaking, any type of polyvinyl chloride is suitable, irrespective of the manner of its preparation. Consequently, polymers obtained, for example, by utilizing bulk, suspension or emulsion processes can be stabilized using the composition according to the invention, irrespective of the intrinsic viscosity of the polymer.

According to the invention, the composition is advantageously utilized in an amount such that the magnesium or calcium acetylacetonate content is between 0.01 and 5 g per 100 g of halogenated polymer, more particularly between 0.05 and 2 g relative to the same reference.

Furthermore, the composition is more particularly utilized in an amount such that the total β-diketone content, in free form and/or in the form of a chelate, is between 0.05 and 1 g per 100 g of halogenated polymer.

In addition to the composition described hereinabove, the formulations based on halogenated polymers can comprise the customary constituent elements of such formulations.

Consequently, the formulations based on halogenated polymer can comprise at least one hydrochloric acid scavenger compound.

The hydrochloric acid scavenger compounds can be of organic type or of inorganic type, and can be present alone or in mixtures.

Among the hydrochloric acid scavengers of organic type, mention may be made more particularly of the compounds comprising an alkaline earth metal or a metal selected from groups IIB, IIA and IVB of the periodic classification of the elements (as it appeared in the supplement to Bulletin de la Societe Chimique de France, No. 1, January 1966).

The cations are more particularly selected, preferably, from calcium, barium, magnesium, strontium, zinc, cadmium, tin and lead.

It should be noted that it is possible to consider using combinations such as, for example, a mixture of hydrochloric acid scavenger based on calcium and zinc, on barium and zinc, or on barium and cadmium, the first combination being preferred.

As far as the hydrochloric acid scavenger compounds of organic type comprising at least one of the elements from groups IIB and IIA are concerned, mention may be made especially of the salts of organic acids, such as aliphatic or aromatic carboxylic acids or fatty acids, or else the aromatic alcoholates or phenolates.

The ones most commonly used are, for example, the salts of the IIA or IIB elements of maleic, acetic, diacetic, propionic, hexanoic, 2-ethylhexanoic, decanoic, undecanoic, lauric, myristic, palmitic, stearic, oleic, ricinoleic, behenic (docosanoic), hydroxystearic, hydroxyundecanoic, benzoic, phenylacetic, para-tert-butylbenzoic and salicylic acids, phenolates, alcoholates derived from naphthol or from phenols substituted by one or more alkyl radicals, such as nonylphenols.

For reasons of practicality or economy, it is preferred to select, from among the abovementioned alkaline earth metal organic compounds, alkaline earth metal propionate, alkaline earth metal oleate, alkaline earth metal stearate, alkaline earth metal laurate, alkaline earth metal ricinoleate, alkaline earth metal docosanoate, alkaline earth metal benzoate, alkaline earth metal para-tert-butylbenzoate, alkaline earth metal salicylate, alkaline earth metal and mono-(2-ethylhexyl) maleate, alkaline earth metal nonylphenates and alkaline earth metal naphthenate, and, from among the abovementioned organocadmium compounds, cadmium propionate, cadmium 2-ethylhexanoate, cadmium laurate, cadmium stearate, cadmium salicylate, cadmium mono(2-ethylhexyl) maleate, cadmium nonylphenates, and cadmium naphthenate.

As regards the compounds of organic type which contain lead, mention may be made in particular of those described in ENCYCLOPEDIA of PVC by Leonard I. Nass (1976), pages 299–303.

These are highly diverse compounds, of which the most commonly used are dibasic lead carbonate, tribasic lead sulphate, tetrabasic lead sulphate, dibasic lead phosphite, lead orthosilicate, basic lead silicate, the coprecipitate of lead silicate and sulphate, basic lead chlorosilicate, the coprecipitate of silica gel and lead orthosilicate, dibasic lead phthalate, neutral lead stearate, dibasic lead stearate, tetrabasic lead fumarate, dibasic lead maleate, lead 2-ethylhexanoate, and lead laurate.

As regards the compounds based on tin, reference may be made in particular to the work "PLASTICS ADDITIVES HANDBOOK" by Gachter/Müller (1985), pages 204–210, or in ENCYCLOPEDIA OF PVC by Leonard I. Nass (1976), pages 313–325.

These are, more particularly, mono- or dialkyltin carboxylates and mono- or dialkyltin mercaptides.

Among these compounds, those used most commonly are the derivatives of di-n-methyltin, di-n-butyltin or di-n-octyltin, such as, for example, dibutyltin dilaurate, dibutyltin maleate, dibutyltin laurate-maleate, dibutyltin bis(mono-$C_4$–$C_8$-alkyl maleate), dibutyltin bis(lauryl-mercaptide), dibutyltin S,S'-(isooctyl mercaptoacetate), dibutyltin β-mercaptopropionate, polymeric di-n-octyltin maleate, di-n-octyltin bis-S,S'-(isooctyl mercaptoacetate), and di-n-octyltin β-mercaptopropionate. The monoalkylated derivatives of the abovementioned compounds are also suitable.

As a hydrochloric acid scavenger of inorganic type, mention may also be made of the sulphates and/or carbonates of aluminium and/or magnesium, especially of the hydrotalcite type. It is recalled that the compounds of hydrotalcite type correspond to the formula $Mg_{1-x}Al_x(OH)_2 A^{n-}_{x/n} \cdot mH_2O$ in which x is between 0 (exclusive) and 0.5, $A^{n-}$ represents an anion such as carbonate in particular, n ranges from 1 to 3, and m is positive. It should be noted that it is possible to utilize products of this type which have undergone a surface treatment with an organic compound. Similarly, it would not be departing from the scope of the present invention to utilize a product of the hydrotalcite type doped with zinc, having optionally undergone a surface treatment with an organic compound. Among products of this type, mention may be made especially of Alcamizer® 4 (marketed by the company Kyowa).

It is also possible to use essentially amorphous compounds of formula $(MgO)_y, Al_2O_3, (CO_2)_x, (H_2O)_z$, in which x, y and z obey the following inequalities: $0<x \leq 0.7$; $0<y \leq 1.7$, and $z \geq 3$. These compounds are described in particular in Patent Application EP 509 864. Moreover, the compounds which are called catoites, of formula $Ca_3Al_2$ $(OH)_{12}$ or else $Ca_3Al_2(SiO)_4(OH)_{12}$, are suitable as hydrochloric acid scavenger compounds of inorganic type.

The formulations based on halogenated polymers may also comprise titanium dioxide.

Preferably, the titanium dioxide is in the rutile form.

Generally, the particle size of the titanium dioxide forming part of the stabilizer compositions according to the invention is between 0.1 and 0.5 $\mu$m.

In accordance with one particular embodiment of the invention, use is made of titanium dioxide in rutile form having undergone a surface treatment, preferably inorganic.

Among titanium dioxides particularly suitable for the utilization of the present invention, mention may be made, without any intention of limitation thereto, of the titanium dioxides Rhoditan® RL 18 and Rhoditan® RL 90, marketed by Rhodia Chimie, and of the titanium dioxides KRONOS 2081® and 2220® marketed by Kronos.

The formulations based on halogenated polymers can also comprise other white or coloured pigments. Among the coloured pigments, mention may be made in particular of cerium sulphide.

It should be noted that the amount of pigment introduced into the formulation varies within wide limits and depends in particular on the colouring power of the pigment and on the final coloration desired. However, by way of example, the amount of pigment can vary from 0.1 to 20 g per 100 g of halogenated polymer, preferably from 0.5 to 15 g relative to the same reference.

The formulation may additionally comprise at least one polyol containing 2 to 32 carbon atoms and having from two to nine hydroxyl groups.

Among these compounds, mention may be made of $C_3$–$C_{30}$ diols such as propylene glycol, butanediol, hexanediol, dodecanediol, neopentyl glycol, polyols such as trimethylolpropane, pentaerythritol, dipentaerythritol, tripentaerythritol, xylitol, mannitol, sorbitol and glycerol, and mixtures of oligomers of glycerol having a degree of polymerization of from 2 to 10.

Another class of polyols which can be utilized appropriately consists of partially acetylated polyvinyl alcohols.

It is possible, likewise, to use hydroxy compounds containing isocyanurate groups, alone or in combination with the abovementioned polyols, such as, for example, tris(2-hydroxyethyl)isocyanurate.

The amount of polyol utilized is generally between 0.05 and 5 g per 100 g of polymer. More especially, it is less than 2 g per 100 g of resin.

It is also possible, if desired, to incorporate into the formulation compounds of the type of organic phosphites, such as, for example, trialkyl, aryl, triaryl, dialkylaryl or diarylalkyl phosphites, in which the term alkyl denotes hydrocarbon groups of $C_8$–$C_{22}$ polyols or monoalcohols and the term aryl denotes aromatic groups of phenol or of phenol substituted by $C_6$–$C_{12}$ alkyl groups. It is also possible to use calcium phosphites, such as, for example, compounds of the type $Ca(HPO_3).(H_2O)$, and also phosphite—hydroxy—aluminium—calcium complexes.

The amount of additive of this type is customarily between 0.1 and 2 g per 100 g of resin.

The formulations may likewise include at least one synthetic crystalline alkali metal aluminosilicate having a water content of between 13 and 25% by weight, of the composition $0.7$–$1M_2O.Al_2O_3.1.3$–$2.4SiO_2$, in which M represents an alkali metal such as, in particular, sodium. Particularly suitable are zeolites of the NaA type, as are described in U.S. Pat. No. 4,590,233.

The amount of this type of compound varies generally between 0.1 and 5 g per 100 g of resin.

The formulations may also include compounds of the epoxide type. These compounds are generally selected from epoxidized polyglycerides, or epoxidized fatty acid esters, such as epoxidized linseed, soya or fish oils.

The amount of compounds of this type varies customarily between 0.5 and 10 g per 100 g of resin.

Other conventional additives may round out the formulation, depending on the application for which it is intended.

As a general rule, the formulation can include phenolic antioxidants, anti-UV agents such as 2-hydroxybenzophenones, 2-hydroxybenzotriazoles or sterically hindered amines, known commonly by the name HALS.

The amount of this type of additive varies generally between 0.05 and 3 g per 100 g of resin.

If necessary, it is also possible to use lubricants which will make it easier to utilize the composition, these lubricants being selected in particular from glyceryl monostearates or else propylene glycol, fatty acids or their esters, montanate waxes, polyethylene waxes or their oxidized derivatives, paraffins, metal soaps, and functionalized polymethylsiloxane oils, such as, for example, $\gamma$-hydroxypropylenated oils.

The amount of lubricant forming part of the formulation based on halogenated polymer varies in general between 0.05 and 2 g per 100 g of resin.

The formulation may also include plasticizers selected from alkyl phthalates. The compounds used most generally are selected from di(2-ethylhexyl)phthalate, the esters of linear $C_6$–$C_{12}$ diacids, trimellitates, and phosphate esters.

The amount of plasticizer employed in the formulations varies within a wide range, depending on the rigid or flexible nature of the final polymer. As an indication, the amount varies from 0 to 100 g per 100 g of polymer.

The formulations can be prepared by any means known to the person skilled in the art.

It is therefore possible to incorporate the various constituents of the polymer, individually or else after having prepared a mixture of two or more of these constituents beforehand; for example, the stabilizer composition of the invention alone or in the presence of lubricant.

The conventional methods of incorporation are ideally suited to producing the formulation based on PVC.

It is therefore possible to conduct this operation in a mixer equipped with a paddle and counter-paddle system operating at a high speed.

Generally, the temperature at which the constituents of the formulation are incorporated is less than 130° C.

Once the mixture has been prepared, the composition is shaped in accordance with the methods which are customary in the art, such as injection moulding, extrusion-blow moulding, extrusion, calendering, or rotomoulding.

The temperature at which shaping is carried out varies in general from 150 to 220° C.

The subject of the present invention is also the use of the composition according to the invention in the shaping of a formulation comprising at least one halogenated polymer for the purpose of preventing the appearance of heterogeneities due to the presence of magnesium or calcium acetylacetonate in the said polymer.

In fact, it has been found, entirely surprisingly, that the incorporation into the halogenated polymer formulation of a composition prepared at the time of use prevented any problem of heterogeneity, whereas the same halogenated polymer formulation comprising calcium acetylacetonate and the $\beta$-diketone, introduced separately at the time of the preparation of the said formulation, did not generally make it possible to prevent such problems.

All of the indications given hereinabove regarding the nature of the various components and their respective proportions remain valid and will not be repeated here.

Specific but nonlimiting examples of the present invention will now be given.

EXAMPLE 1

1/ Preparation of a Mixture Comprising Zinc and Calcium Acetylacetonate

Calcium acetylacetonate (1 mol) and zinc acetylacetonate (2 mol) are introduced into a high-speed paddle mixer apparatus.

Mixing is carried out in dry form from the powders, at a temperature of the order of 60° C.

The resulting product, which is in the form of a white to cream-coloured powder, has a melting point of 170° C. as measured on a Kofler bench.

2/ Use of the Mixture in a PVC Formulation Pigmented with Carbon Black (a) The Composition of the Black Masterbatch is as Follows:

| | |
|---|---|
| Lacovyl GV 13/10 ® PVC resin (Solvay) | 100 parts |
| Calcium stearate | 0.25 part |
| Carbon black | 0.25 part |
| Dioctyl phthalate | 29 parts |
| Tinstab BM271 ® (Ackros Chemicals) | 0.2 part |
| Lubricant | 0.5 part |

The powders are mixed in a Hobart® mixer (Kenwood planetary type) for 30 minutes.

The liquid compounds are subsequently added over 30 minutes with stirring at a temperature of 50° C.

Stirring is continued at 50° C. for 1 hour.

(b) Calendering

The black masterbatch obtained above is utilized on a Troester® roll-type mixer:
- firstly, with the mixture obtained in section 1/ above (E1, in accordance with the invention) and
- secondly, with calcium acetylacetonate (E2, comparative).

Features of the Apparatus:
- Troester® twin-roll mixer type WNK 1 No. 1355;
- Rolls: diameter: 101 mm; length: 250 mm.
- The rolls rotate at a speed of 29 rpm;
- The friction ratio is 1/1 (friction coefficient zero);
- The roll temperature is 175° C.

Procedure 100 g of the black masterbatch obtained in section 1/ are gelled on the Troester® roll-type mixer.

After 90 seconds of calendering, with the spacing of the rolls then being set at 0.7 (1 mm sheet thickness), 2.5 g of acetylacetonate are added (on the one hand in the form of the sample E1, on the other hand in the form of the sample E2).

Finally, a passage "to the end" is carried out with a roll spacing of 0.4.

After calendering for 210 seconds, a sheet of 1 mm in thickness (roll spacing at 0.7) is withdrawn and the sheets obtained are cooled.

The calendered sheets are compared visually. The number of white spots appearing on the black background of the sheet characterizes the state of dispersion of the calcium acetylacetonate.

No visible agglomerates or pinholes are observed in the case of the sheet comprising the sample E1 according to the invention, whereas they do exist on the sheet comprising the comparative sample E2. This demonstrates, consequently, a better dispersion of the composition according to the invention in the polymeric formulation.

EXAMPLE 2

This example concerns the preparation of a mixture containing calcium acetylacetonate and zinc dibenzoylmethanate.

The procedure of Example 1 is repeated except that a powder mixture is prepared from calcium acetylacetonate (1 mol) and zinc dibenzoylmethanate (1 mol).

The melting point of the resulting mixture is 183° C. as measured on a Kofler bench.

EXAMPLE 3

This example concerns the preparation of a mixture containing calcium acetylacetonate and a mixture of free β-diketones.

The procedure of Example 1 is repeated except that a powder mixture is prepared from calcium acetylacetonate (50 parts by weight) and a 70/30 mixture of stearoylbenzoylmethane and palmitoylbenzoylmethane (50 parts by weight).

The melting point of the resulting mixture is less than 180° C. as measured on a Kofler bench.

This example is applicable for the products of rhodiastab® 50 and rhodiastab® X5 type.

What is claimed is:

1. A composition having a melting point of less than or equal to 200° C. and comprising:
   (a) a magnesium or a calcium acetylacetonate; and
   (b) at least one free β-diketone of the following formula (I):

wherein:
   $R^1$ and $R^3$ identical or different represent a substituted or unsubstituted linear or branched $C_1$–$C_{30}$ hydrocarbon radical and $R^2$ represents a hydrogen atom or a linear or branched $C_1$–$C_4$ hydrocarbon radical; or
   (b') at least one β-diketone in the form of a chelate of the formula (II)

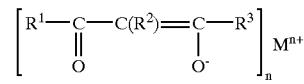

wherein $R^1$, $R^2$, and $R^3$ are as defined above, $M^{n+}$ is lanthanum, magnesium, aluminium, zinc or calcium, n being 2 or 3, with the proviso that acetylacetonates of calcium and of magnesium are excluded.

2. A composition according to claim 1, wherein $R^1$ and $R^3$ represent a linear or branched $C_1$–$C_{24}$ alkyl; a linear or branched $C_1$–$C_{24}$ alkenyl radical; a $C_6$–$C_{30}$ aryl group, optionally substituted by at least one alkyl radical, one halogen atom or one silicon atom; or a $C_3$–$C_{14}$ cycloaliphatic radical, optionally containing carbon—carbon double bonds.

3. A composition according to claim 2, wherein $R^1$ and $R^3$ represent a linear or branched $C_1$–$C_{18}$ alkyl radical; a $C_6$–$C_{10}$ aryl radical, optionally substituted by at least one alkyl radical or one halogen atom; or a $C_3$–$C_{14}$ cycloaliphatic radical, optionally containing carbon—carbon double bonds.

4. A composition according to claim 1, wherein the weight ratio between (a) and (b) or (b') is between 1/10 and 10/1.

5. A composition according to claim 4, wherein the weight ratio is between 1/6 and 6/1.

6. A composition according to claim 1, wherein the β-diketone is in chelate form.

7. A process for the preparation of a composition as defined in claim 1, comprising the steps of:
   1) homogenizing a mixture of magnesium or calcium acetylacetonate and the β-diketone in free form or in chelate form.

8. A process according to claim 7, further comprising the steps of:
   2) grinding said mixture.

9. A process according to claim 7, wherein step 1) is carried out at a temperature of between 20 and 100° C.

10. A process according to claim 9, wherein the temperature is between 50 and 100° C.

11. A process for heat stabilizing a halogenated polymer formulation, comprising the step of adding to said formulation a composition as defined in claim 1.

12. A process according to claim 11, wherein the composition is added in an amount such that the magnesium or calcium acetylacetonate content is between 0.01 and 5 g per 100 g of said halogenated polymer formulation.

13. A process according to claim 12, wherein the magnesium or calcium acetylacetonate content is between 0.05 and 2 g per 100 g.

14. A process according to claim 12, wherein the composition is added in an amount such that the total β-diketone content, free or in the form of a chelate, is between 0.05 and 1 g per 100 g of said halogenated polymer composition.

15. A composition according to claim 1, further comprising polivinyl chloride.

16. A process according to claim 11, wherein said halogenated polymer is polivinyl chloride.

17. A process according to claim 13, wherein said halogenated polymer is polivinyl chloride.

* * * * *